(12) United States Patent
Hiroura et al.

(10) Patent No.: US 10,117,601 B2
(45) Date of Patent: Nov. 6, 2018

(54) ACTIVITY STATUS MEASURING DEVICE

(71) Applicant: FBTriangle Co., Ltd., Tokyo (JP)

(72) Inventors: Masatoshi Hiroura, Tokyo (JP); Yutaka Saho, Tokyo (JP)

(73) Assignee: FBTRIANGLE CO., LTD., Tokyo (JP)

( * ) Notice: Subject to any disclaimer, the term of this patent is extended or adjusted under 35 U.S.C. 154(b) by 184 days.

(21) Appl. No.: 15/152,519

(22) Filed: May 11, 2016

(65) Prior Publication Data

US 2016/0332026 A1 Nov. 17, 2016

(30) Foreign Application Priority Data

May 13, 2015 (JP) .................... 2015-098439

(51) Int. Cl.
| | |
|---|---|
| *A61B 5/11* | (2006.01) |
| *A61B 5/00* | (2006.01) |
| *A61B 5/117* | (2016.01) |
| *A61B 5/05* | (2006.01) |
| *G06F 19/00* | (2018.01) |
| *H01Q 1/22* | (2006.01) |

(52) U.S. Cl.
CPC .......... *A61B 5/1118* (2013.01); *A61B 5/0002* (2013.01); *A61B 5/0507* (2013.01); *A61B 5/117* (2013.01); *A61B 5/6891* (2013.01); *A61B 5/6892* (2013.01); *G06F 19/3481* (2013.01); *H01Q 1/2225* (2013.01); *A61B 5/742* (2013.01); *A61B 5/746* (2013.01); *A61B 2503/10* (2013.01)

(58) Field of Classification Search
CPC ... A61B 2503/10; A61B 5/1118; A63B 5/118; A63B 5/0002; A63B 5/6892; A63B 5/117; A63B 5/6891; A63B 5/0507; A63B 5/742; A63B 5/746; G06F 19/3481
See application file for complete search history.

(56) References Cited

U.S. PATENT DOCUMENTS

| | | | |
|---|---|---|---|
| 2003/0227386 A1 | 12/2003 | Pulkkinen et al. | |
| 2006/0217603 A1* | 9/2006 | Nagai | A61B 5/1118 |
| | | | 600/323 |

(Continued)

FOREIGN PATENT DOCUMENTS

JP 2001314378 11/2001

*Primary Examiner* — Jasson Yoo
(74) *Attorney, Agent, or Firm* — Porzio Bromberg & Newman (57) ABSTRACT

A plurality of wireless vital sensors for capturing biometric data of individuals is laid out and fixed at predetermined setting locations. The vital sensors are configured to sense the biometric data of an individual via non-contact when the individual enters the sensing area of any one of the plurality of vital sensors. Moreover, there is no discomfort while the wireless vital sensor is attached or no risk of damage to or destruction of the wireless vital sensor due to collisions during games. Additionally, the measuring device also includes the identification sensors for identifying a mobile object, and the individual corresponding to the biometric data sensed by the vital sensors is identified by the RFID data from the identification sensor. Accordingly, in a configuration where the wireless vital sensors can capture the biometric data of an unspecified number of individuals, which individual the biometric data belongs to can be surely identified.

4 Claims, 6 Drawing Sheets

(56) References Cited

U.S. PATENT DOCUMENTS

| | | |
|---|---|---|
| 2008/0096726 A1 | 4/2008 | Riley et al. |
| 2008/0113772 A1 | 5/2008 | Burrill et al. |
| 2009/0227882 A1 | 9/2009 | Foo |
| 2009/0270170 A1 | 10/2009 | Patton |
| 2010/0240999 A1* | 9/2010 | Droitcour ................ A61B 5/05 600/453 |
| 2012/0075103 A1 | 3/2012 | Powell et al. |
| 2012/0253484 A1 | 10/2012 | Burich et al. |
| 2013/0080185 A1* | 3/2013 | Picard .................. A61B 5/0022 705/2 |
| 2014/0364141 A1 | 12/2014 | O'Hagan et al. |

\* cited by examiner

| vital sensor ID | RFID |
|---|---|
| 1 | A-1 |
| 2 | A-2 |
| ⋮ | ⋮ |
| 6 | A-6 |
| 7 | B-1 |
| 8 | B-2 |
| ⋮ | ⋮ |
| 12 | B-6 |
| ⋮ | ⋮ |

FIG. 4A

|  | ID | player's name |
|---|---|---|
| Group A | A-1 | Jhon |
|  | A-2 | Mike |
|  | ⋮ | ⋮ |
|  | A-6 | Eric |
| Group B | B-1 | Smith |
|  | ⋮ | ⋮ |

FIG. 4B

| vital sensor ID | measurement data | | | | | |
|---|---|---|---|---|---|---|
| 1 | 250 | 248 | 249 | ... | ... | ... |
|  | 100 | 98 | 97 | ... | ... | ... |
| 2 | 240 | 235 | 234 | ... | ... | ... |
|  | 99 | 89 | 90 | ... | ... | ... |
| 3 | ⋮ | ⋮ | ⋮ | | | |
|  | ⋮ | ⋮ | ⋮ | | | |

ACTIVITY STATUS MEASURING DEVICE

FIELD OF THE INVENTION

The present invention relates to a measuring device for obtaining the activity status of an individual using biometric data (vital sign data) such as body temperature, breathing, pulse, blood pressure and the like of the individual, measured by sensors. The present invention particularly relates to assisting decision-making as to which individuals should be put on a team in order to improve the overall group performance of the team in cases where a plurality of individuals participate to engage in a team activity.

DESCRIPTION OF THE RELATED ART

For example, a plurality of individuals form a team to engage in a soccer or ice hockey game, and compete against an opposing team. Individual performance is dependent on the physical condition and degree of anxiety of each individual on game day; and performance also drops due to the accumulation of fatigue with the passing of game time. In the case of group physical activity, a decrease in the performance of a single player might lead to a decrease in the performance of other players on the same team, which significantly affects the overall performance of the team.

If each individual accurately obtained his own physical condition by himself and communicated the condition (e.g. having a high fever that prevents them from achieving expected performance in competition, etc.) to their manager or coach prior to the game, a substitute player could participate in the team. Additionally, even when a player is healthy or a good condition, fatigue accumulates easily when the activity level of the player in the game is high or when the game is being held in extremely hot or extremely cold environments. Thus, every player experiences a drop in performance, even if there are differences in degree. Regardless, players rarely request substitution for the reason of accumulation of fatigue during a game. As such, the managers and the coaches must carefully observe the activity status of each player and determine when to make substitutions at the proper timing. However, it is not easy to determine the substitution timing and/or which bench player to use as the substitute.

Accordingly, systems have been conventionally developed that track and manage performance by monitoring the activity status and physical state during exercise of individuals (e.g. see U.S. Patent Publication No. 2008/0096726A1). Treadmills installed at sporting centers and the like are also configured to measure and display the heart rate or the like of an individual on a display screen. Furthermore, devices for improving the overall performance of a team have also been proposed (e.g. see European Patent Publication No. 2682052A2). These devices or systems monitor measurement data captured by a biometric data measuring device attached to the arm or leg of each individual, and attempt to provide a user with useful information by processing the measurement data.

SUMMARY OF THE INVENTION

However, in general, it is not preferred that players wear any biometric data measuring devices directly attached to their bodies during a game. One reason is that monitoring during competition is different than monitoring activity during practice and players may experience a sense of discomfort when a body-contact-type of measuring device is attached to their bodies. Additionally, when the measuring device may become displaced due to body movement, replacement is required. As a result, the player will not be able to focus on the game. Another reason is that there is heavy contact between players in soccer, ice hockey, and the like, which gives rise to a risk of damage to or failure of the body-contact-type of measuring device.

Accordingly, it would be desirable to measure biometric data that shows the activity status of individuals using non-contact sensors, and assist the decision-making as to how great the degree of change is compared to normal times.

With the measuring device of the present invention, a plurality of wireless vital sensors for capturing biometric data of individuals is laid out and fixed at predetermined setting locations. Additionally, the wireless vital sensors are configured to sense the biometric data of an individual via non-contact when the individual enters the sensing area of any one of the plurality of wireless vital sensors. Therefore, there is no need to attach wireless vital sensor to the bodies of each individual. Moreover, there is no discomfort while the wireless vital sensor is attached or no risk of damage to or destruction of the wireless vital sensor due to collisions and the like during games.

Each of the wireless vital sensors does not a personal monitoring sensor for measuring biometric data of an individual such as player. Rather, the wireless vital sensors are fixed at the predetermined setting location and each of wireless vital sensors may measure an unspecified player that comes close to wireless vital sensors. In other words, there is no need to provide a number of wireless vital sensors equal to the number of members of the group or team because the wireless vital sensor functions as a monitoring sensor for any individual that could be a member of the group or team. Accordingly, only the minimum number of wireless vital sensors required for be set in response to the type of sports so that costs can be reduced.

Additionally, the measuring device of the present invention comprises the identification sensors for identifying or recognizing a mobile object in addition to the wireless vital sensors, and the individual corresponding to the biometric data sensed by the wireless vital sensors is identified by the ID data from the identification sensor. Accordingly, in a configuration where the wireless vital sensors can capture the biometric data of an unspecified number of individuals, which individual the biometric data belongs to can be surely identified.

The measuring device of the present invention communicates a converter on a communication network, and the converter may associate the biometric data captured by the wireless vital sensors with the ID data captured by the identification sensors, and also performs the preprocessing of the data required by the applications running on the data processing terminal (e.g. a mobile device) displaying the biometric data. As a result, applications for displaying the player's performance data on the data processing terminal that receives data from the converter will be easily developed, and the load associated with running these applications can be greatly reduced.

This Summary is provided for purposes of summarizing some exemplary embodiments to provide a basic understanding of aspects of the subject matter described herein. Accordingly, the above-described features are merely examples and should not be construed to narrow the scope or spirit of the subject matter described herein in any way. Other features, aspects, and advantages of the subject matter described herein will become apparent from the following Detailed Description, Figures, and Claims.

BRIEF DESCRIPTION OF THE DRAWINGS

A better understanding of the present invention can be obtained when the following detailed description of the embodiments is considered in conjunction with the following drawings.

DETAILED DESCRIPTION OF THE EMBODIMENTS

Hereinafter, preferred embodiments of the present invention will be described while referring to the drawings.

The present embodiment illustrates an example in which the measuring device of the present invention is applied to the sport of ice hockey. The present embodiment is aimed to measure the biometric data of players participating in the sport of ice hockey and, thereby, facilitate the best overall performance of the team.

Figure 1A:
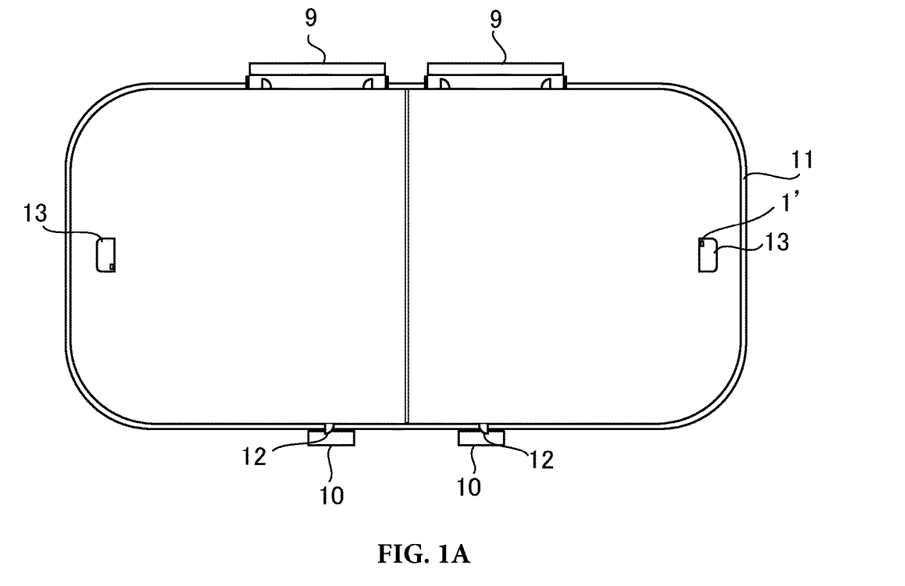
FIG. 1A illustrates an example activity status measuring device of according to one embodiment of the present invention installed in a sporting facility.

Ice hockey is a team (group) sport played on a natural or artificial ice skating rink, in which players wear ice skates. In many cases a team, including starting and bench players, consists of about 18 to 22 roster (registered) players including two goaltenders. As illustrated in FIG. 1, the periphery of the rink where the sport is played is surrounded by a fence-like enclosure called a board 11. The manager, coach, and players enter a player's bench 9 at rink-side (except when in a penalty bench 10).

The rules dictate that each team can have a maximum of six players on the ice at any time. Faster speeds are reached compared to other similar sports played on fields due to the use of skates, which makes the game thrilling, but due to the high risk of contact and the like, players are required to wear protective gear. Additionally, due to the characteristics of the sport, namely having high activity levels by the players and fatigue being easily accumulated, it is difficult to play ice hockey continuously for an extended duration of time. As such, the offensive and defensive teams (except goaltenders) are organized in advance into groups called "sets-units-lines" and the groups are substituted on the fly during the game approximately every minute. In other words, the game progresses with a six-person group comprising a goaltender being substituted for another group approximately every minute. During the substitution time, players can sit down at the player's bench 9 of their own team at rink-side and recover stamina, and wait for the timing of the next substitution. Note that the player's bench 9 has a bench length of 10 meters or greater and a width of 1.5 meters or greater so as to accommodate the players and team officials.

Figure 1B:
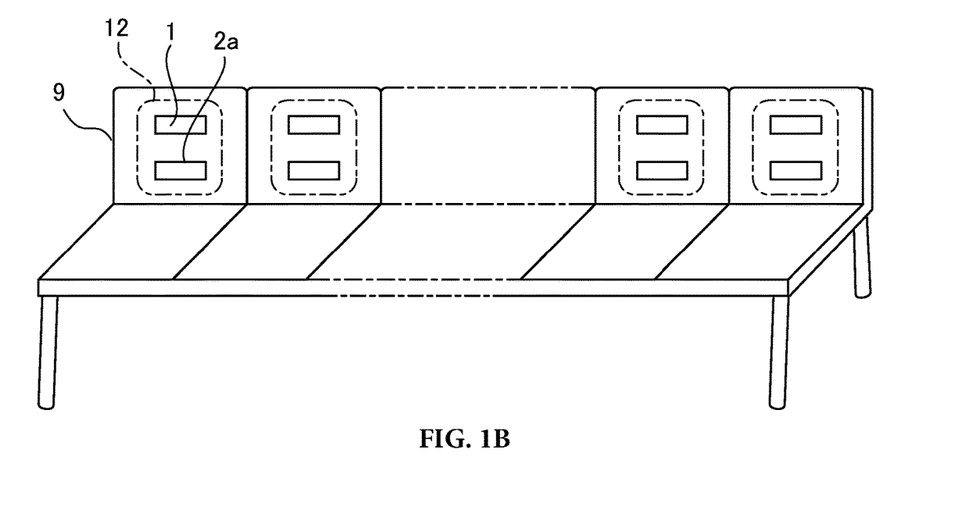
FIG. 1B illustrates an example identification sensor and an example vital sensor and placed in a player's bench used in an ice hockey game.
Figure 3:
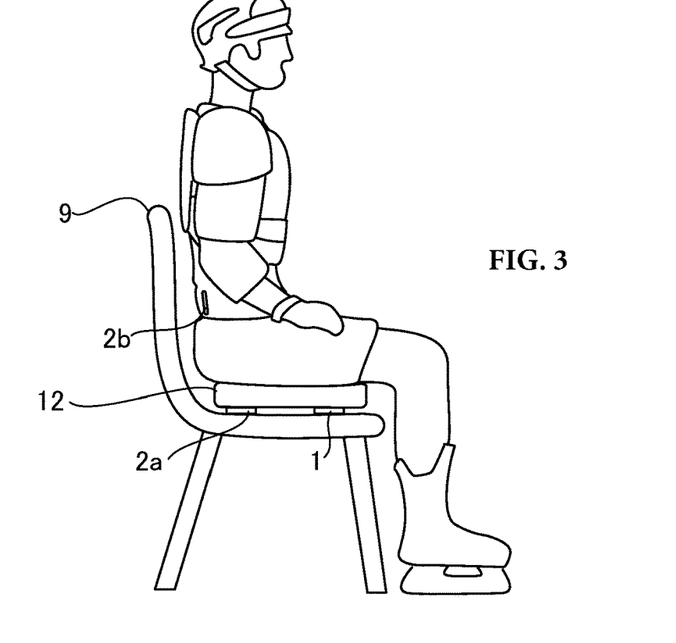
FIG. 3 is illustrates a situation where a player are sitting down on a bench so that signals are transmitted between the vital sensor and the identification sensor identification sensor according to another embodiment.

A wireless vital sensor 1 used in a measuring device 100 of the present embodiment is set on the player's bench 9 as illustrated in FIG. 1. In FIG. 1, the wireless vital sensor 1 is set on a backrest surface of the bench but, as illustrated in FIG. 3, may also be set on a seat surface. In actuality, worsening of the sitting comfort of the bench due to the presence of the wireless vital sensor 1 can be prevented by placing a cushion member 12 on the backrest surface or the seat surface.

In the case of the measuring device 100 of the present embodiment, at least six of the wireless vital sensor 1 are set on the player's bench 9. This is to comply with the rule that each team can only have a maximum of six players on the ice at any time in the sport of ice hockey. When the six players on the ice return to the player's bench 9 for substitution, they as guided to sit at the locations where the wireless vital sensors 1 are set. Note that when 18 players are registered, they are organized into three groups. One group (with six players) is either on the ice or the penalty bench, and the other two groups (12 players) are standing by. Accordingly, 12 of the wireless vital sensors 1 may be set on the player's bench 9. Additionally, the wireless vital sensors 1 may be attached to the board 11 (i.e. the fence wall around the rink), together with hereinafter described identification sensors 2. Alternatively, the wireless vital sensors 1 may be divided, a portion being set on the player's bench 9 and the remaining portion being attached to the board 11.

When players on the ice return to the player's bench 9 for substitution and enter a sensing area (e.g. when they sit on the bench), the wireless vital sensors 1 sense their biometric data. The wireless vital sensor 1 of the present embodiment has a Doppler sensor configuration in which weak microwaves are emitted and the difference between the emitted wave and the reflected wave is detected. Pulse data, breathing data and the like is filtered and extracted from the difference with sensed reflected wave. Given that the output of PHS devices used in hospitals and the like is 80 mW, the output of the wireless vital sensor 1 is weak at 10 mW or less. Moreover, the frequency of the micro radio waves of the wireless vital sensor 1 is, for example, 24 GHz, a higher frequency than the 0.8 to 2.4 GHz radio waves used by a wireless LAN, mobile phones, and the like. Therefore, the microwaves of the wireless vital sensor 1 pose less harm to the human body as they will reflect off the surface of the human body and not enter the body. Furthermore, by limiting the emission direction of the microwaves to a predetermined range, the wireless vital sensor 1 can be calibrated to not sense the biometric data of the player sitting adjacent on the bench and high-accuracy data can be secured.

Additionally, identification sensors 2 (2a and 2b) used in the measuring device 100 of the present embodiment are RFID sensors that transmit data wirelessly between an RF tag 2b embedded with ID data and an RFID receiver 2a such as an RFID reader located near the RF tag 2b. The type of tag (passive tag, active tag, or the like), transmission method (electromagnetic induction method, radio wave method, or the like), and communication method are not particularly limited and can be selected as desired.

Figure 4A:
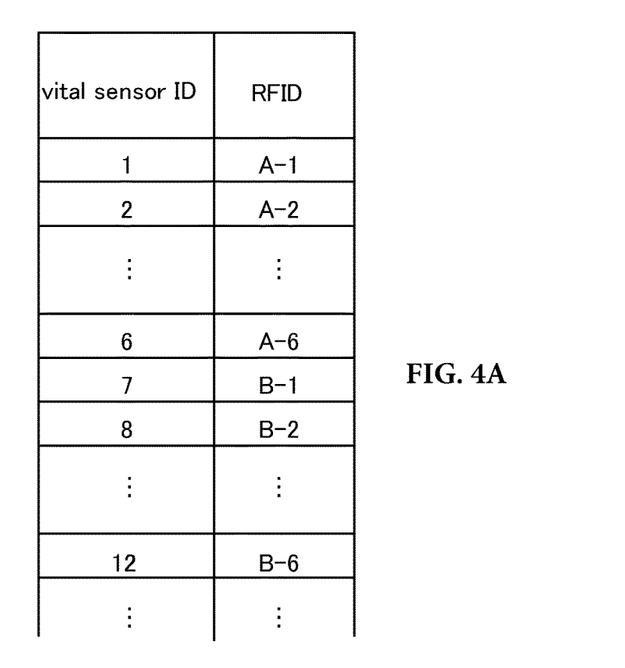
FIG. 4A is an exemplary table for showing a relationship between the vital sensor and the identification sensor.
Figure 4B:
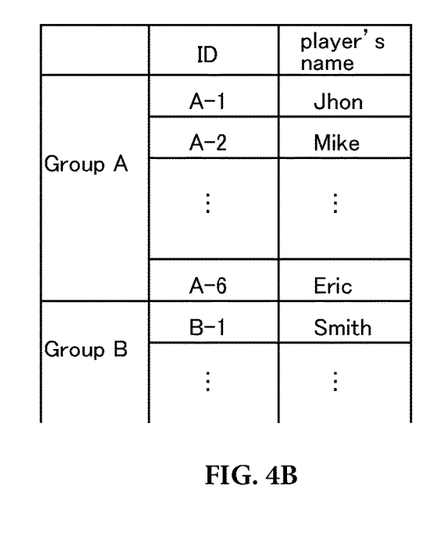
FIG. 4B is an exemplary table for showing a relationship between ID data of the identification sensor and each player's name.

A plurality (in the embodiments, six as mentioned above) of the RFID receiver 2a of the identification sensor 2 is set near the vital sensors 1 on the player's bench 9. Correspondence as to which of the wireless vital sensors 1 each of the identification sensors 2 is paired with is set in advance as illustrated in FIG. 4A. Furthermore, correspondence identifying which player the ID data belongs to is also set in advance (see FIG. 4B).

Figure 1C:
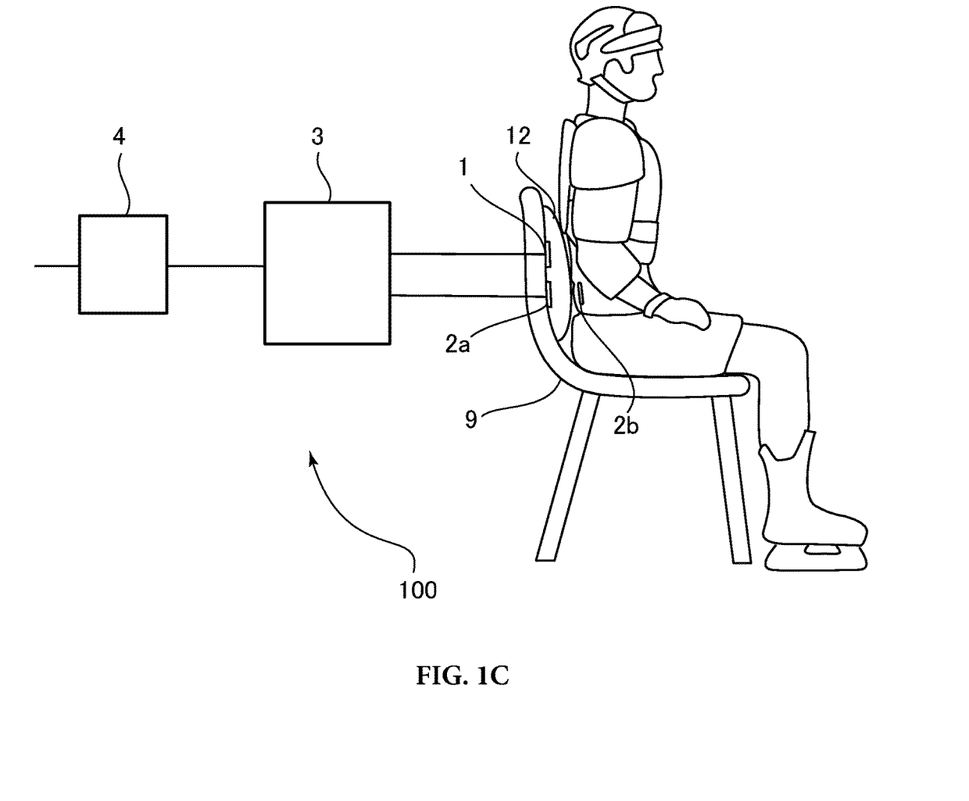
FIG. 1C illustrates a situation where a player are sitting down on a bench so that signals from the vital sensor and the identification sensor is transmitted to the a mobile router via a data converter.

In the present embodiment, as with the wireless vital sensors 1, each of the identification sensors 2 is set on the backrest surface of the player's bench 9. The RF tag 2b of each of the RFID receivers 2a is sewn or attached or in another way to the back surface of the uniform, protective gear, or underwear of each player. In the present embodiment, the RF tag 2b is attached on an inner side (body side) of protective gear for protecting the upper body of a player, specifically, the portion guarding the spine area. Note that in FIGS. 1C and 3, for ease of illustration, the RF tag 2b is attached to the underwear or the like of the player, and a state with the uniform removed is illustrated. While it is possible to attach the RF tag 2b to the glove, helmet, or other protector, it is preferable that the RF tag 2b be attached to the uniform, protective gear, or underwear as players may remove their helmets and the like during the game while waiting on the player's bench 9. Particularly, in cases where the RFID receiver 2a is set on the backrest of the bench, when the RF tag 2b is attached on the back side of the body of the player, communication degradation between the RF tag 2b and the RFID receiver 2a can be minimized. Note that in another embodiment, as with the wireless vital sensor 1 illustrated in FIG. 3, the RFID receiver 2a may be set on the seat surface or alternatively may be set above the player, which is a ceiling direction.

The ID data identifying the player is stored in the RF tag 2b attached to the uniform or the like of the player. Therefore, the RF tag 2b can transmit the ID data of the player wirelessly to the RFID receiver 2a. When a player on the ice enters the player's bench 9 and sits or begins to sit, the RFID receiver 2a receives the ID data transmitted from the RF tag 2b. As a result, the RFID receiver 2a can reliably identify which player has sat on the player's bench 9.

Just as with the wireless vital sensor 1, the directionality of the radio waves of the RF tag 2b and the RFID receiver 2a must be calibrated in order to maximize the elimination of noise between the RF tag 2b and the RFID receiver 2a of the identification sensor 2, and also so that the ID data of the player sitting adjacent on the bench is not detected.

Figure 2:
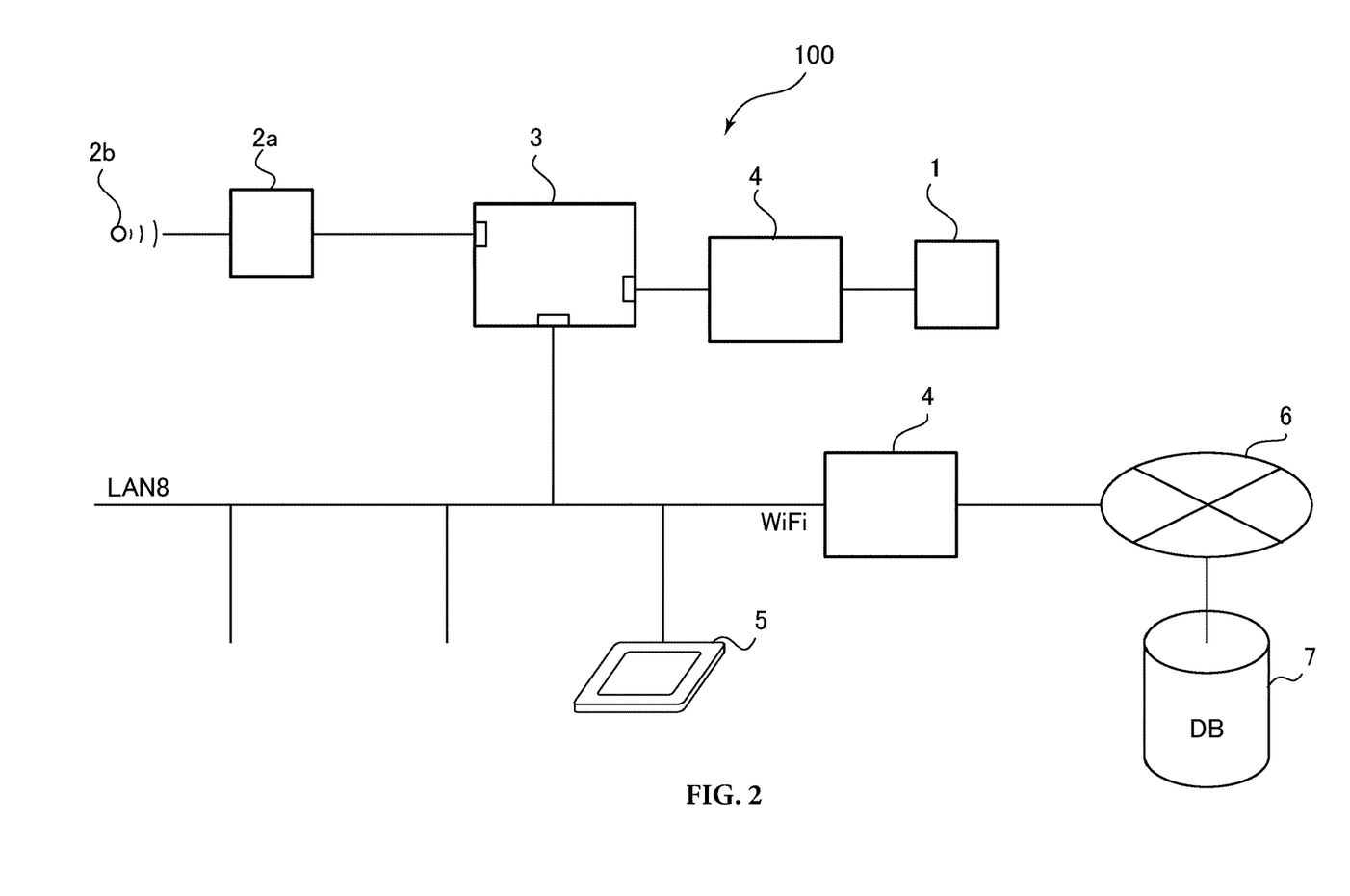
FIG. 2 is an example block diagram of a system comprising the measuring device.

FIG. 2 illustrates an example of a configuration of a communications network of the present embodiment. The biometric data of each player sensed by the wireless vital sensor 1 is transmitted via a mobile router 4 to a LAN port of a converter 3 located on a wireless LAN 8. The mobile router 4 located between the wireless vital sensor 1 and the converter 3 is provided in order to assign an IP address to each of the wireless vital sensors 1. The ID data of the player transmitted from the RF tag 2b and received by the RFID receiver 2a of the identification sensor 2 is transmitted to a serial port of the converter 3 via an RS232 or similar serial interface. As described above, the correspondence as to which of the wireless vital sensors 1 each of the identification sensors 2 is paired with is set in advance as illustrated in FIG. 4A. Therefore, the converter 3 can associate the biometric data from the wireless vital sensor 1 with the ID data from the identification sensor 2. In other words, tagging of which player the biometric data belongs to is carried out in the converter 3.

Figure 4C:
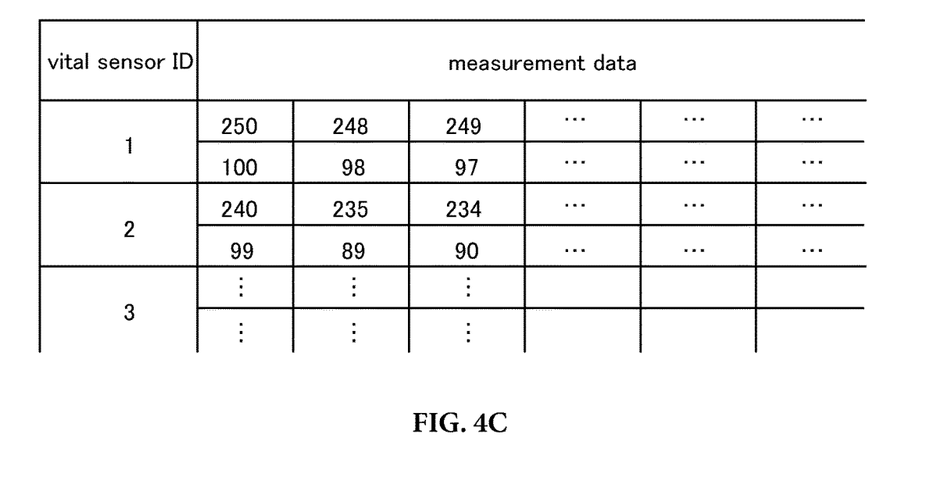
FIG. 4C is illustrates an example of biometric data captured by the vital sensor.

As such, the biometric data of an individual player can be obtained using a pair of the wireless vital sensor 1 and the identification sensor 2. In the present embodiment, six of such pairs are provided, so the biometric data of six individual players can be captured simultaneously, provided that the six players sit on the player's bench 9 at approximately the same time. While the corresponding RF tag 2b and RFID receiver 2a are exchanging ID data, each of the wireless vital sensors 1 continuously senses the pulse and breathing of the players and captures the biometric data at a predetermined time interval (e.g. every three seconds). FIG. 4C illustrates an example where the wireless vital sensor 1 captures the biometric data of each player every three seconds. The upper part of measurement data shows the heart rate and the bottom part shows the respiratory rate. In another embodiment, biometric data may be captured from the start of wireless communication between the RF tag 2b and the RFID receiver 2a to the passing of a predetermined amount of time (e.g. one minute).

Note that the wireless vital sensor 1 can determine whether or not a player is seated on the player's bench 9. Thus, even in cases where interference occurs due to the RFID receiver 2a of the identification sensor 2 responding to the RF tag 2b of an adjacent player who is not yet seated, misbehavior of the RFID receiver 2a can be detected through a comparison with the seated time from the wireless vital sensor 1, and data accuracy can be increased.

Furthermore, the player in charge of the goaltender position is not substituted out as frequently as the other players in the same group but, just as with the other players, the performance of the goaltender drops with the passage of game time. As such, the biometric data of the goaltender can be captured by attaching a wireless vital sensor 1' to a top portion of the goal frame, at a position where the goaltender can be sensed. In cases where the goaltender is to be identified using the RFID receiver 2a, the RFID receiver 2a is preferably set on the top portion of the goal frame, the same as the wireless vital sensor 1.

The converter 3 performs the tagging of which player the biometric data belongs to and, thereafter, transmits the biometric data to an information processing terminal 5 connected to the wireless LAN 8 via a different LAN port than the LAN port used for the biometric data from the wireless vital sensor 1. The information processing terminal 5 is a mobile terminal held by a manager or coach in the sporting facility. Additionally, by bringing the mobile router 4 into the sporting facility, the information processing terminal 5 will be constantly connected to a public line such as an internet 6 via the WiFi-connected mobile router 4 during the game. A plurality of networks using different LAN ports are configured to be used in the converter 3 in order to prevent the introduction of noise from other lines. As such, if the converter 3 is used in an environment free of noise interference, a configuration is possible in which the biometric data from the wireless vital sensor 1 is input to the converter 3 and output to the information processing terminal 5 via the same LAN port. Note that in cases where the sporting facility is not equipped with a network environment, the information processing terminal 5 may connect to the internet 6 using a public mobile phone network. In this case, the converter 3 may be connected to the mobile phone network and perform network communications via a mobile router or mobile data card connected to the converter 3.

Upon the information processing terminal 5 receiving the biometric data of each player from the converter 3 via the wireless LAN 8, an application running on the information processing terminal 5 processes the biometric data and displays the processing results, thereby assisting substitution decisions made by the manager or the like and improving the overall performance of the team. In addition to processing the biometric data of the players in the game alone, the application can also process the biometric data of the players in the game while referencing biometric data during regular practice. The biometric data during practice is stored in advance in a database 7 and, for example, consists of biometric data of each player under different circumstances such as daily average heart rate and average respiratory rate, average heart rate and respiratory rate after a predetermined time (e.g. one minute) of exercise, average heart rate and average respiratory rate during sleep, and the like. When the application running on the information processing terminal 5 issues a query request for the biometric data of a player stored in the database 7 connected with the internet 6 during a game, the application compares the biometric data received from the converter 3 (short-term biometric data) with the biometric data stored in the database 7 (long-term biometric data) and displays it on-screen. Thus, it is possible to obtain how much the heart rate and/or respiratory rate have risen.

Furthermore, penalties are imposed on players or teams that commit infractions based on the weight of the infraction. The referee removes the offending player from the ice and detains him in a penalty box 10 (see FIG. 1). When the penalty time has expired, the player can exit the penalty box 10 and return to the ice. Management of players entering and exiting of the penalty box 10 can be performed and time spent in the penalty box 10 and time spent on the ice can be measured by the RFID receiver 2a of the identification sensor 2 set on a gate 12 of the penalty box 10.

Figure 5:
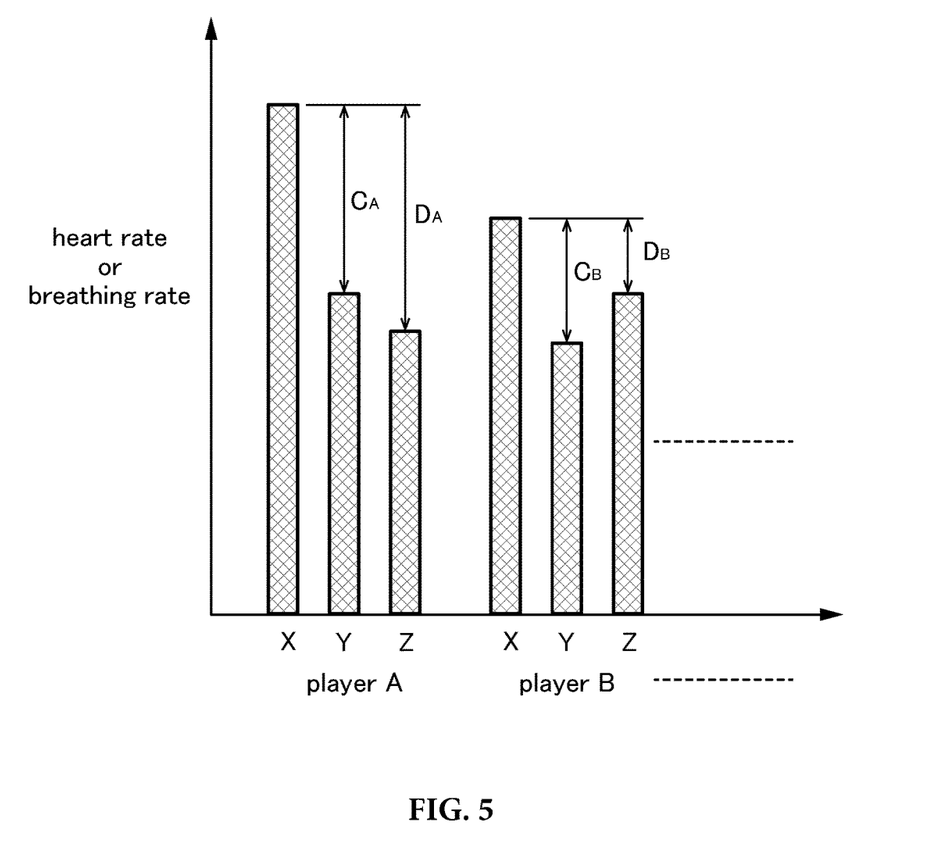
FIG. 5 is an exemplary graphical output on a display processed by an software application that is run on a user device.

FIG. 5 illustrates a display example of processing results output by the application. Respiratory rates and heart rates that have risen due to exercise gradually decrease through post-exercise rest so as to approach a pre-exercise state. As the rate of decrease depends on the congenital physical ability, amount of practice, and the like of each player, how the rates decrease will not be the same for all players. Thus, as illustrated in FIG. 5, for each player, the heart rate and respiratory rate immediately after returning to the bench (X values) and the post-rest (e.g. after one-minute) heart rate and respiratory rate (Y values), are lined up and displayed in a manner so that the post-rest rate of decrease can be compared. For example, the rate of decrease of the heart rate of player A after one-minute (difference: $C^A$) is extreme and the heart rate of players B does not display as significant a change (difference: $C_B$) as player A. In other words, $C_A > C_B$. A decrease in the exercise-induced increased heart rate and/or respiratory rate indicates a recovery of stamina and, therefore, the processing results shown in FIG. 5 indicate that the amount of fatigue accumulated decreased as a result of player A taking a one-minute rest. In other words, player A has a fast rate of fatigue recovery. On the other hand, the processing results shown in FIG. 5 indicate that fatigue still remained even after player B took a one-minute rest. Degrees of fatigue recovery such as these can be quickly obtained. Accordingly, these processing results facilitate to decide whether to send the group with players A and B out on the ice in their current configuration at the next opportunity or if a player needs to be substituted out and, if substituting, with which players should be substituted. As a result, it is easy for the manager to make the decision to substitute another player for player B.

Furthermore, as described above, the information processing terminal 5 receives the average heart rate and average respiratory rate after the predetermined time (e.g. one minute) of exercise of each player with the query request to the database 7. These biometric data are measured by attaching the wireless vital sensor 1 during regular practice as well, and are stored as statistical values.

Accordingly, the application may be configured to not only simply compare the amounts of decrease in heart rate and respiratory rate of players after one-minute during a game, but also may be configured to compare players that have lower amounts of decrease in heart rate and the like (in other words, players with accumulated fatigue), using the average heart rates and average respiratory rates after one-minute of exercise stored in the database 7 as a reference for comparison with regular practice. For example, as illustrated in FIG. 5, in a comparison of the amount of decrease of the heart rate after one-minute rest of player A and player B, having returned to the player's bench 9 during a game, it is clear that the amount of decrease of player A is greater than that of player B ($C_A > C_B$). Therefore, it is conceivable that player A has recovered more stamina. However, when the average heart rates after one-minute of exercise $D_A$ and $D_B$, which are stored in advance in the database 7, are factored in, it becomes clear that the heart rate of player A has not decreased significantly compared to the expected amount of decrease $D_A$ as measured in regular practice and that the amount of decrease of the heart rate of player B is actually greater than in regular practice.

Accordingly, it is preferable not to simply compare the lower amounts of decrease in the heart rates $C_A$ and $C_B$ after one-minute on game day, but to normalize them using lower amounts of decrease in the average heart rates after one-minute of exercise $D_A$ and $D_B$, which are stored in advance in the database 7, to provide the actual degree of stamina recovery on game day.

Preferably, instant comparisons are made possible through line graphs, color-coded displays, and the like in addition to histograms in order to enable the manager to make decisions in a short period of time. Furthermore, referencing the average values of the stored biometric data, a threshold value may be preset where performance will drop if a player continues to exercise in excess thereof, and a display or alert may be provided on the display screen so that the manager or the like will easily understand that the threshold has been exceeded.

Preferably, a value suitable for each player is set as the threshold. Thus, the convenience of the manager or the like using the information processing terminal 5 will be greatly enhanced because the biometric data will be processed in various ways in the application.

Additionally, when a player becomes a top athlete, overseas competitions become more frequent and the management of the physical condition of the player becomes more difficult due to jet-lag and the like. Through experience, it is known that players with jet-lag tend to have higher body temperatures and elevated heart rates. As such, the biometric data at night of each player is monitored one day or multiple days prior to game day. Specifically, for example, the wireless vital sensor 1 is set under the mattress of the bed of the player and the heart rate and respiratory rate are sensed. The wireless vital sensor 1 can distinguish whether or not the player is in bed because it senses if the player gets out of bed. Moreover, the wireless vital sensor 1 can sense continuous data of body movement (rolling over) in real-time.

Body temperature can be measured using a thermometer at a predetermined time (e.g. immediately before bedtime), or may be measured by setting a thermal infrared sensor (not illustrated) on the ceiling or the like of the room. The thermal infrared sensor has a temperature sensor function in which the temperature of a light receiving element rises as a result of absorbing infrared radiation. Therefore, by measuring the infrared radiation emitted in accordance with each body temperature of the body and converting the measurements into electric signals, the temperature (body temperature) can be detected without touching the body.

Accordingly, prior to the game or during the game, the manager or the like can use the information processing terminal 5 to view the results of comparing the heart rate and the obtained changes in body temperature sensed by the wireless vital sensor 1 with the regular heart rate and body temperature of the player stored in the database 7 and obtain if the player still is suffering from jet-lag and if there is a risk of the player not achieving their best performance.

Note that in cases where only one player sleeps in a room, the player can be identified without using the identification sensor 2, but this should not be construed as a limitation on the use thereof. For example, in cases where multiple players share a room designed for two or more people, in practicality it is difficult to determine in advance which player is being sensed by the wireless vital sensor 1. Thus, by using the identification sensor 2, the biometric data of each player can be sensed regardless of which bed each player uses.

However, the information processing terminal 5 cannot easily process the biometric data in the state transmitted from the converter 3 in real-time. In cases where the display of the heart rate and the respiratory rate needs to be updated every one to three seconds, the refresh period will be short and the load will be great. As the number of sensors increases, the load becomes even more prominent. Being able to convert the biometric data into a form of data that can be easily read and written by the application will lead to enabling updating of the display at short intervals.

Accordingly, the converter 3 of the present embodiment is provided with a JavaScript Object Notation (JSON) conversion function for converting the measurement data to JSON format in the converter 3 itself. JSON is based on Java® script used in web browsers and the like and, therefore, the data converted to JSON format can be easily read using Java® script.

The biometric data converted to JSON format by the JSON conversion function of the converter 3 can be passed to the information processing terminal 5 in real-time. Because data from many sensors can be aggregated and passed to the application side at short intervals, there is no need for data acquisition settings in peer-to-peer (sensor-application) mode for each individual sensor.

Additionally, as described above, the association of the biometric data sensed by the wireless vital sensor 1 and the ID data of the identification sensor 2 is carried out on the converter 3 side, and it is easy to determine which player the data belongs to. For example, with a configuration where the biometric data and the ID data are captured individually and associated using a web-based server, there are other various processes being executed as server functions (e.g. retry transmissions due to noise errors, interrupt handling from other tasks, and the like) and the processing becomes complicated and delayed. Therefore, data handling is easier by addressing these tasks using the converter 3. These benefits get greater as the number of sensors increases.

In the present embodiment, the biometric data can be read and written through simple processing as converted JSON data. Therefore, processing will be speedy and applications for running on the information processing terminal 5 can be easily developed. Furthermore, with the converter 3 provided with the JSON conversion function, the data can be aggregated and sent and, as a result, each individual application will not need to send multiple access requests to the sensor side such as the wireless vital sensor 1 or the identification sensor 2. Therefore, there are merits in that the transmission load can be lightened and battery depletion of the sensors can be reduced.

Furthermore, an example using an acceleration sensor will be described. An example where the RFID receiver 2a of the identification sensor 2 was set in the gate 12 of the penalty box 10 was described above. Because the rules dictate that the penalty box 10 may only be entered or exited through the gate 12, confirmation as to whether the player that was in the penalty box 10 has returned to the ice can be performed with only the RFID receiver 2a. Entering and exiting of each player to and from the player's bench 9 can also be managed by setting the RFID receiver 2a in the gate of the player's bench 9, but sometimes players do not pass through the gate and instead jump over the board 11, which is a fence, to return to the player's bench 9 or to return to the ice. As such, it may not be possible to accurately manage entering and exiting to and from the player's bench 9.

Therefore, it is preferable to also use an acceleration sensor to complement the management of entering and exiting based on reception results of the RFID receiver 2a. That is, just as with the RF tag 2b, if an acceleration sensor (not illustrated) is attached to the protective gear of each player, the field intensity of the players on the player's bench 9 will be constant and the field intensity of players on the ice will fluctuate depending on the location of the player. As such, it is preferable to check whether or not a player is on the ice by looking at the field intensity from the acceleration sensor and, along with the reception results from the RFID receiver 2a, determine whether a player is on the player's bench 9.

Furthermore, with the acceleration sensor, it is possible to measure distance traveled, maximum speed, average speed, and travel path on the ice (trace map) of each player as well as the number of times each player touched the puck (number of hits) and the number of shots each player had on the goal 13. The various data measured by the acceleration sensor can be transmitted to the converter 3 via the wireless LAN 8 in the sporting facility just as with the wireless vital sensor 1 and the identification sensor 2, and the activity status of each player can be comprehensively obtained from a variety of angles.

Thus, according to the present invention, it is possible to objectively and quantitatively obtain whether each player is performing as expected and a manager or the like can easily determine which individuals from among a plurality of individuals to add or remove as members forming a group. As a result, the system can assist to improve the overall performance of the group and in future train to increase stamina.

The embodiments described above illustrate examples where the present invention is applied to players of ice hockey, but it is obvious that the present invention can also be applied to other team sports such as soccer, volleyball, and the like. In soccer, volleyball, and the like, multiple players are not substituted out sequentially as a group like in ice hockey. Instead, the players gather around the manager on the court during half-time, time outs, and other breaks. Preferably, these breaks are used to obtain the activity status of each player with the measuring device 100 including the wireless vital sensor 1 and the player's bench 9.

Additionally, in addition to sports, in situations where a plurality of people assemble in a given area such as in a hospital or nursing station (especially in emergencies) and it is not determined where each individual is in a particular bed or a particular stretcher, an activity status measuring device using the wireless vital sensors, the identification sensor, and the converter of the present invention can be used to reliably obtain the biometric data of each individual. Thus, the present invention is a technology with high industrial use.

Embodiments of the present invention may be realized in any of various forms. For example, in some embodiments, the present invention may be realized as a computer-implemented method, a computer-readable memory medium, or a computer system. In other embodiments, the present invention may be realized using one or more custom-designed hardware devices such as ASICs. In other embodiments, the present invention may be realized using one or more programmable hardware elements such as FPGAs.

In some embodiments, a non-transitory computer-readable memory medium may be configured so that it stores program instructions and/or data, where the program instructions, if executed by a computer system, cause the computer system to perform a method, e.g., any of a method embodiments described herein, or, any combination of the method embodiments described herein, or, any subset of any of the method embodiments described herein, or, any combination of such subsets.

In some embodiments, a user device may be configured to include a processor (or a set of processors) and a memory medium, where the memory medium stores program instructions, where the processor is configured to read and execute the program instructions from the memory medium, where the program instructions are executable to implement any of the various method embodiments described herein (or, any combination of the method embodiments described herein, or, any subset of any of the method embodiments described herein, or, any combination of such subsets). The device may be realized in any of various forms.

Although the embodiments above have been described in considerable detail, numerous variations and modifications will become apparent to those skilled in the art once the above disclosure is fully appreciated. It is intended that the following claims be interpreted to embrace all such variations and modifications.

What is claimed is:

1. A measuring device comprising:
a plurality of wireless vital sensors fixed at adjacent predetermined setting locations, wherein the wireless vital sensors are configured to simultaneously sense biometric data of each individual of a set of individuals with non-contact for a predetermined time upon entry of the individual into a sensing area of any one of the plurality of vital sensors, and wherein the wireless vital sensors are configured to repeatedly sense the biometric data of individuals when the individual gets out from the sensing area according to passing of the predetermined time and then again enters into the sensing area of any one of the plurality of vital sensors;
a plurality of identification sensors, and each of the identification sensors comprising a transmitter and a receiver to wirelessly transmit ID data of the individual,
wherein the receiver is positioned near one of the wireless vital sensors corresponding to the receiver and each of the wireless vital sensors is preliminarily associated with the receiver in one of the identification sensor to make a pair, and the receiver accepts the ID data from the transmitter upon entry of the transmitter that is attached to the individual into a coverage area of the receiver; and
a converter for determining that the biometric data sensed by the wireless vital sensor associated with the receiver for a time period of accepting the ID data of the receiver is for the individual identified by the ID data based on a relationship between the receiver and the wireless vital sensor, and sending to an information processing terminal.

2. The measuring device of claim 1, wherein the converter is configured to convert the ID data and the associated biometric data to a format of JavaScript Object Notation (JSON) prior to send to the information processing terminal.

3. A performance assessment system comprising:
a plurality of wireless vital sensors fixed at predetermined setting locations, wherein the wireless vital sensors are configured to sense biometric data of individuals with non-contact upon entry of the individual into a sensing area of any one of the plurality of vital sensors,
a plurality of identification sensors, and each of identification sensors comprising a transmitter and a receiver to wirelessly transmit ID data of the individual,
wherein the receiver is positioned near one of the wireless vital sensors corresponding to the receiver and each of the wireless vital sensors is preliminarily associated with the receiver in one of the identification sensors, and the receiver accepts the ID data from the transmitter upon entry of the transmitter that is attached to the individual into a coverage area of the receiver; and
a converter for determining that the biometric data sensed by the associated wireless vital sensor associated with the receiver for a time period of accepting the ID data of the receiver is for the individual identified by the ID data based on a relationship between the receiver and the wireless vital sensor to make a pair, and an information processing unit for comparing the biometric data of the individual from the converter with corresponding biometric data stored of the individual to analyze change of performance for the individual.

4. The performance assessment system of claim 3, wherein the information processing unit is configured to represent a predetermined display or alert when the change of performance surpasses a predetermined threshold.

* * * * *